United States Patent [19]

Matsumoto

[11] Patent Number: 4,952,049
[45] Date of Patent: Aug. 28, 1990

[54] APPARATUS FOR MEASURING THE REFRACTION OF EYE

[75] Inventor: Kazuhiro Matsumoto, Kawasaki, Japan

[73] Assignee: Canon Kabushiki Kaisha, Tokyo, Japan

[21] Appl. No.: 237,161

[22] Filed: Aug. 29, 1988

Related U.S. Application Data

[63] Continuation of Ser. No. 848,973, Apr. 7, 1986, abandoned.

[30] Foreign Application Priority Data

Apr. 12, 1985 [JP] Japan .................................. 60-77938

[51] Int. Cl.$^5$ ................................................ A61B 3/10
[52] U.S. Cl. ..................................... 351/211; 351/205
[58] Field of Search ................. 351/205, 206, 211, 212

[56] References Cited

U.S. PATENT DOCUMENTS 4,283,124 8/1981 Matsumura ......................... 351/206
4,293,198 10/1981 Kohayakawa et al. ............. 351/211
4,421,391 12/1983 Matsumura et al. ................ 351/211

FOREIGN PATENT DOCUMENTS 55-110531 2/1979 Japan .
6018153 7/1983 Japan .

Primary Examiner—Paul M. Dzierzynski
Attorney, Agent, or Firm—Fitzpatrick, Cella, Harper & Scinto

[57] ABSTRACT

An eye refractometer comprising a projection optical system for projecting an index mark onto an eye fundus of an eye to be examined through a first aperture stop disposed substantially conjugate with the pupil of the eye, a measuring optical system for guiding to a light-position detecting device the light beam of the index mark reflected from the eye fundus through a second aperture stop disposed substantially conjugate with the pupil and a device for calculating the refractive value of the eye from the output of the light-position detecting device, at least one of the first and second aperture stops having an area type opening.

11 Claims, 3 Drawing Sheets

APPARATUS FOR MEASURING THE REFRACTION OF EYE

This application is a continuation of application Ser. No. 848,973 filed Apr. 7, 1986, now abandoned.

BACKGROUND OF THE INVENTION

1. Field of the Invention

This invention relates to an apparatus for measuring the refraction of eye (eye refractometer) for use in ophthalmic hospitals, opticians or the like.

2. Related Background Art

A conventional refractometer of the type to which the present invention is pertinent is disclosed, for example, in the specification of U.S. Ser. No. 755,362 of the present application. The refractometer is provided with a projection optical system for projecting an index mark onto the eye fundus of an eye to be examined through a first aperture stop disposed substantially conjugate with the pupil of the eye, and a measuring optical system for guiding, to light-position detecting means, the light beam of the index mark reflected from the eye fundus through a second aperture stop disposed substantially conjugate with the pupil of the eye. The first and second aperture stops have each three spot openings arranged on an arc and extending in three meridian directions. The positions of the three spot openings are determined so when they are projected on the pupil of the eye to be examined, the respective images of the spot openings will be symmetric to the optical axis in the three meridian directions.

However, it has been found that the above-mentioned type of refractometer is unsatisfactory in the following points: the apparatus cannot give information of eye refraction other than that in three meridian directions; measurement errors tend to be caused especially when the measured eye is of irregular astigmatism; extremely high precision is required in setting the light-position detector means in the three meridian directions.

SUMMARY OF THE INVENTION

Accordingly, it is an object of the present invention to provide an eye refractometer which is able to afford more eye refraction information so as to enable it to measure the refraction of an eye with a high degree of accuracy even for an irregular astigmatism.

It is another object of the present invention to provide an eye refractometer in which the arrangement of light-position detecting means can be very easily made and a high degree of accuracy of measurement can be assured every time.

It is a further object of the present invention to provide an eye refractometer which enables the examiner to observe and understand the information of the refraction of the examined eye in a simple manner through a monitor by identifying the shape on the monitor.

It is still another object of the present invention to provide an eye refractometer having basically no movable portions.

DESCRIPTION OF THE PREFERRED EMBODIMENT

Figure 1:
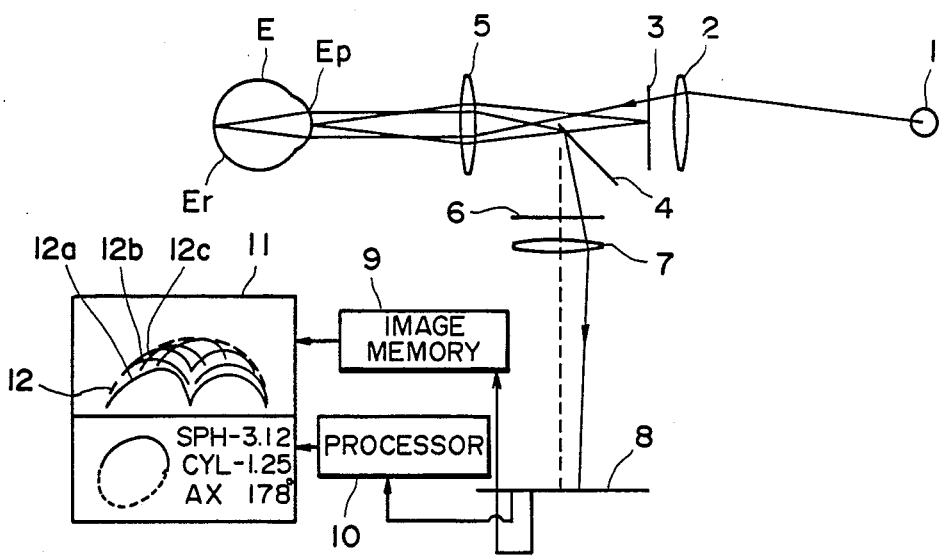
FIG. 1 shows the construction of a first embodiment of the present invention.

Referring to FIG. 1 schematically showing a first embodiment of the present invention, an eye to be measured is designated by E and a spot light source serving as a measurement index mark by 1.

Figure 2:
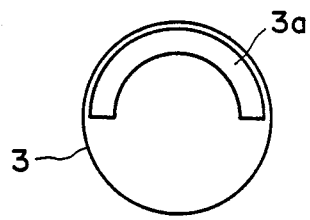
FIGS. 2 and 3 are front views of first and second aperture stops respectively.
Figure 3:
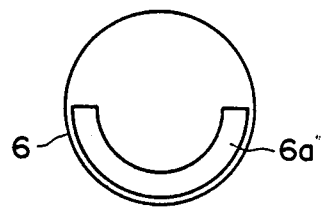

On the optical axis extending from the light source 1 to the eye E, there are arranged, in succession from the light source side, a first lens 2, a first aperture stop 3 and an objective lens 5. These elements constitute a projection optical system. The first aperture stop is at a position substantially optically conjugate with the pupil Ep of the eye E. A mirror 4 is provided in the lower half area of the optical path between the first aperture stop 3 and the objective lens 5. On the refraction side of the mirror 4 there are arranged a second aperture stop 6, a second lens 7 and a light-receiving surface 8. These elements constitute a measuring optical system. The second aperture stop 6 is also at a position substantially conjugate with the eye pupil. As shown in FIGS. 2 and 3, the first aperture stop 3 has an area type opening 3a and the second aperture stop 6 has an area type opening 6a.

Both of the area type openings 3a and 6a are in the form of a semicircular ring and they have a common center near the optical axis. The images of the openings 3a and 6a projected on the eye E have the same outer diameter. Unlike the conventional spot type opening, the area type opening has a certain size of area which cannot be regarded as a spot. Different points in the area type opening correspond to spot type openings arranged in different meridian directions.

The light emitted from the light source 1 passes through the first lens 2, the opening 3a of the first aperture stop 3 and the area above the mirror 4. Further being transmitted through the objective lens 5, the projected light forms an image of the light source on the fundus Er of the eye E. The reflected light from the eye fundus Er runs back toward the objective lens 5. After passing through the objeicve lens, the reflected light is deflected downwardly by the mirror 4. The reflected light reaches the light-receiving surface 8 passing through the opening 6a of the second aperture stop 6 and the second lens 7. The light-receiving surface 8 is disposed substantially conjugate with the light source 1.

The output from the light-receiving surface 8 is displayed on the upper area of the screen of a monitor 11 through an image memory 9. As will be described in detail later, images 12a, 12b and 12c in the form of an upper half of an ellipse serially appear on the upper area or the monitor 11. The imaginary envelope 12 is analogous to the image and also describes a semi ellipse. The size of the semi-ellipse of the envelope 12 is proportional to the degree of short-sightedness (myopia) or long-sightedness (hyperopia). The size of the semi-ellipse decreases gradually with approaching to orthoscopic. If the eye E is an orthoscopic eye, the semi-ellipse becomes a point. For an astigmatic eye, the envelope is elliptic. For an eye without astigmatism, the envelope is a regular circle. Discrimination between myopia and hyperopia can be made by whether the semi-ellipse is appearing with the chord upward or downward.

On the lower half of the screen of the monitor 11 there are displayed the results obtained by calculations from the output of the light-receiving surface 8 by the processor 8, namely, the degree of sphericality, the degree of astigmatism and the angle of astigmatism. Furthermore, the envelope 12 is displayed there.

Each of the semi-ring openings 3a, 6a in the above-shown embodiment may be considered as an expansion along an arc of the conventional three spot openings in three meridian directions. Therefore, the information obtained by the embodiment is not limited to that only in the three meridian directions, but information in any directions can be obtained. Furthermore, it is no longer necessary that the light-receiving surface 8 be particularly formed of linear position sensors arranged in three meridian directions as in the case of the conventional ones. These features of the present invention will hereinafter be described further theoretically by reference to FIGS. 4 to 10.

Figure 4:
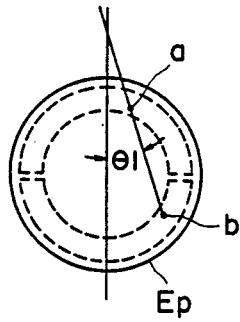
FIGS. 4 and 7 are views illustrating the relation between an incidence position and an exit position of a light beam on a pupil of an eye to be examined.
Figure 5:
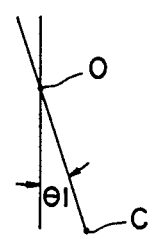
FIGS. 5 and 6 are views illustrating a position at which the light beam arrives on a light-receiving surface.

The position at which the light is received by the light-receiving surface 8 is determined both by the distance between the incidence and exit points of the light on the pupil Ep of the eye E to be examined, and by the angle which the connecting line between the incidence and exit points forms with respect to a reference direction. As an example, let the sphericality be D, and the degree and the angle of astigmatism of the eye E be O. For this eye E, if the measuring light enters the pupil Ep at the point a and exits from the point b as shown in FIG. 4, then the light will be received by the light-receiving surface 8 at the point C in FIG. 5. Herein, $\theta$, is the angle which the segment a-b forms with respect to the reference direction (in the shown example, the reference direction is the vertical direction). Point O in FIG. 5 is a point at which an image of the index mark is formed. In this example, the point O corresponds to the position of the light source and therefore to the position of the optical axis. The distance from the point O to the light receiving point C, that is, the length of the segment O-C is proportional to the length of the segment a-b. Also, the angle which the segment O-C forms with respect to the reference direction is equal to the angle $\theta$, which the segment a-b forms with respect the reference direction. When the first and second aperture stops 3 and 6 have semi-circular ring openings 3a and 6a with their common center being in the vicinity of the optical axis as previously shown in FIGS. 2 and 3, the light ray which arrives at the remotest point from the point O is the ray which enters the opening from the outermost point and emerges from it at the opposite outermost point symmetrical to the entrance point about the center. However, herein, the size of the light source is not taken into consideration.

Figure 6:
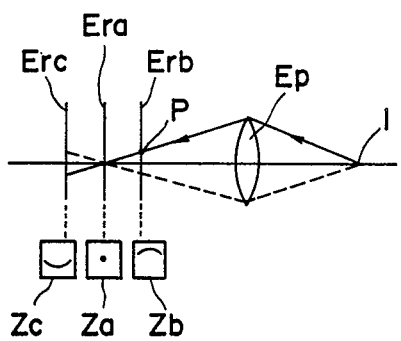

The above will be understood more clearly from the example shown in FIG. 6 wherein Era, Erb and Erc represent the funduses of an orthoscopic eye, a hyperopic eye and a myopic eye respectively. Za, Zb and Zc are images of the light source 1 on the respective eye funduses.

As seen from FIG. 6, in the case of a hyperopic eye, as an example, the point P at which the light spot on the eye fundus Erb is the furthest from the optical axis is formed by the light ray which is the furthest from the optical axis also on the pupil Ep. As previously shown, the light from the light source 1 is projected onto the fundus of the eye to be examined through the area type first aperture stop 3. Therefore, when the eye is not orthoscopic, the light image formed on the fundus of the eye has a form corresponding to the refractive power of the examined eye. An image of the same form as the image on the eye fundus has is projected onto the light-receiving surface 8 through the second aperture stop 6.

The outline of the image of the light source 1 formed on the light-receiving source 8 in this manner is formed by those rays which enter the opening of the first aperture stop 3 at its outer-diametric points and emerge from the opening of the second aperture stop 6 at its outer-diametric points as an infinite number of elliptic envelopes 12a, 12b, 12c . . . . . . shown in FIG. 1. All of these rays have the same distance to the entrance point and to the exit point. Therefore, the distance between the point O and the outline of the image varies in proportion to the refractive power of the examined eye. But, since the eye to be examined usually has some astigmatism, the rays shift in the direction normal to the meridian direction to an extent corresponding to the degree of astigmatism. The connecting line of the incident points of these rays describes an ellipse as a rule for the following reason.

Figure 7:
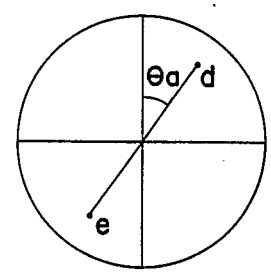

The distance between the point O and the outline of the image is proportional to the refractive power of the examined eye E. Let the proportional constant be $\alpha$, the angle of astigmatism of the eye E be $\theta$, the diopter in the direction of astigmatism axis be D1 and the diopter in the direction normal to the astigmatism axis be D1. Further, assuming that a diametrically furthermost light ray enters the eye at the point d and emerges from it at the point e as shown in FIG. 7, let the angle the segment d-e forms with the reference direction be $\theta a$. Then, the ray will fall upon the light-receiving surface at the point P shown in FIG. 8.

Figure 8:
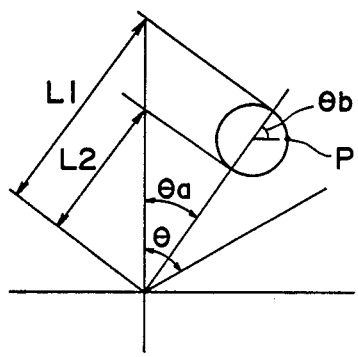
FIG. 8 is a view illustrating a position at which the light beam arrives on the light-receiving surface in the case where the examined eye is astigmatic.
Figure 9:
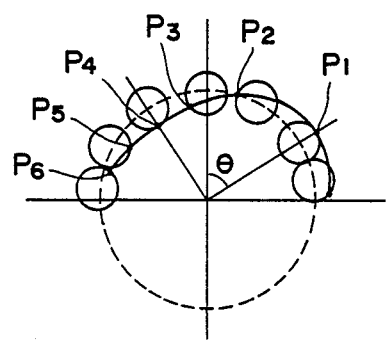
FIGS. 9 and 10 are views illustrating a contour of image on the light-receiving surface.

In FIG. 8, the origin of the coordinates is the above-mentioned point P. L1 is equal to $\alpha D1$ and L2 to $\alpha D2$. The angle $\theta b = 2(\theta - \theta a)$. Further, the point P is on the circumference of a circle which has a radius of $(L1-L2)/2$ and whose center is at the point $[\{(L1+L2)/2\} \sin \theta a, \{(L1+L2)/2\} \cos \theta a]$. When the angle $\theta a$ is rotated by 180 degrees, that is to say, when any arbitrary angle $\theta a$ is considered as illustrated in FIG. 9, the locus that the point P describes forms an ellipse F as shown in FIG. 10.

Figure 10:
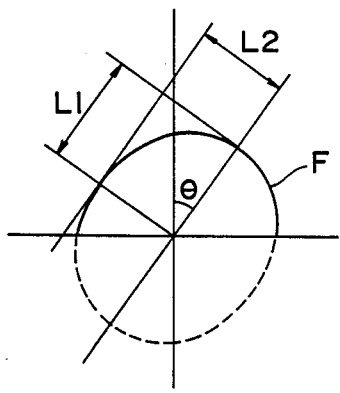

In the ellipse F shown in FIG. 10, the radius in the major axis direction L1 is equal to $\alpha D1$ and that in the minor axis direction is equal to $\alpha D2$. Further, the ellipse F is inclined by the angle $\theta$ relative to the reference direciton.

It will be readily seen from the foregoing that if we can know the shape of the ellipse F, we can determine the sphericality, the degree of astigmatism and the angle of astigmatism axis. Consequently, we can obtain all of necessary information about the refractive power of the eye to be examined E by providing a two-dimensional light position detector device on the light-receiving surface 8 to measure the major and minor axes of the elliptic image as well as the inclination of the ellipse from the distribution of intensity of the light on the light-receiving surface. Thus, even for an irregular astigmatic eye, an accurate measurement of eye refractive power can be assured. As another advantage, the examiner can catch the information of the eye refractive power in a very simple and convenient manner by observing the shape of the image on a monitor display as illustrated in FIG. 1.

As the light-receiving surface 8, there may be used also one-dimensional light position detector devices arranged parallel with each other in place of a two-dimensional position detector.

In the conventional apparatus, spot-shaped openings have been used as the openings of the aperture stops. Because of it, one-dimensional position sensors in the conventional apparatus have been required to be arranged very accurately in meridian direction aligned with the spot openings. In contrast, according to the present invention where area type openings are used, such a high degree of accuracy of alignment is unnecessary for the setting of one-dimensional light position detector devices. Even when the accuracy of the alignment is low, the apparatus according to the present invention does not fail to detect the information about the refractive power of the examined eye.

In order to determine the shape of an ellipse F, it is generally necessary to know the coordinates of five points. This means that it is possible to determine the shape of an ellipse F by use of five one-dimensional light position detector devices. In this connection, it is to be understood that the shape of the F may be determined also from the coordinates of three points. The reason for this is that when the light source 1 serving as an index mark on the optical axis is projected onto the fundus of the eye to be examined, the center of the ellipse of the light source image can be considered not to shift from the optical axis.

Figure 11:
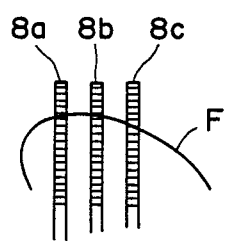
FIG. 11 shows an example of the light-receiving surface formed of one-dimensional position sensors.

FIG. 11 shows an example of the arrangement of light position detectors to determine the shape of the ellipse F. In this example, three linear light-position sensors 8a, 8b and 8c are used, which are arranged in three parallel lines.

Figure 12:
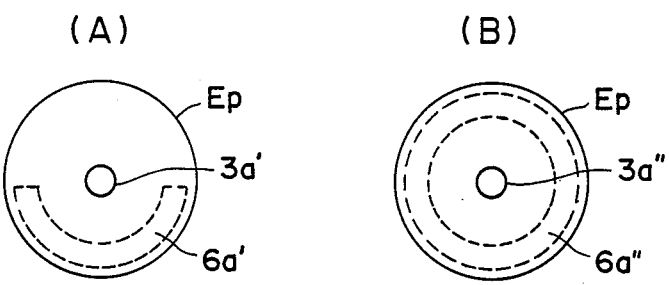
FIGS. 12(A) and 12(B) illustrate other embodiments of the aperture stops.

In the above embodiment, the first aperture stop 3 in the projection optical system and the second aperture stop 6 in the measuring optical system have been shown to have similar semi-circular ring openings with their common center being near the optical axis. However, it is to be understood that various modifications are possible in the form of the area type openings. A modification is shown in FIG. 12A. In this modification, the first aperture stop 3 has a spot type opening 3a' whereas the second aperture stop 6 has an area type opening 6a' in the form of a part of a ring. The center of the ring lies at the spot opening 3a'. The semi-ring opening 6a' may have any arbitrary segment angle about the center.

In another modification shown in FIG. 12B, the opening of the first aperture stop 3 is in the form of a spot and that of the second aperture stop 6 is an area type opening in the form of a ring whose center is at the spot opening. As a further modification, the openings of the first and second aperture stops 3 and 6 may be exchanged with each other.

While the light source 1 itself has been as used the index mark in the above embodiment, the index mark may also be formed by projecting a beam of light on a pin hole or the like.

Figure 13:
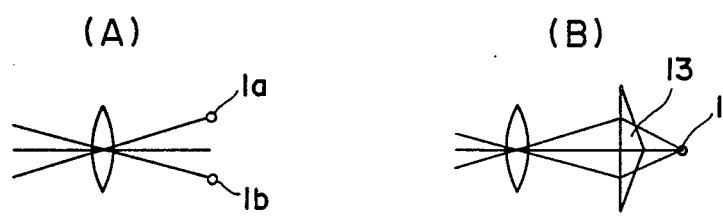
FIGS. 13(A) and 13(B) show other embodiments in which substantially a plurality of light sources are used.

In respect to the light source 1 serving as an index mark also, various modifications are possible. For example, instead of a single light source 1 there may be provided two or more light sources at a position or positions on the optical axis and at an off-axial position or positions within a plane normal to the optical axis. By increasing the number of light sources in this manner, the accuracy of measurement can further be improved. FIG. 13A shows a modification where two light sources 1a and 1b are provided at off-axial positions in a plane normal to the optical axis. FIG. 13B shows still a further modification where a prism 13 is interposed in the optical path from a light source 1 provided on the optical axis. The prism 13 has the effect to apparently change the single light source on the optical axis into a plural number of light sources (for example, two light sources) symmetrically arranged about the optical axis.

Figure 14:
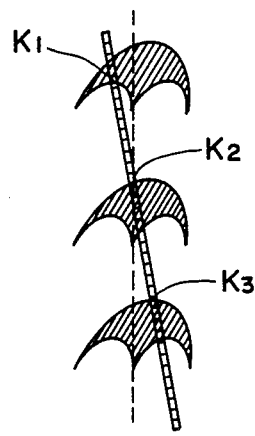
FIG. 14 shows another embodiment in which a single one-dimensional position sensor is used to identify the shape of an image.

When a plural number of light sources are provided, a plural number of light source images are also formed. In this case, a plurality of one-dimensional light position detectors are generally required to detect the shape of the ellipse then formed. However, it is also possible to detect the shape of the ellipse by use of single one-dimensional position detector in the manner shown in FIG. 14. In the embodiment shown in FIG. 14, the shape of the elliptical light source image is detected from intersections $K_1$, $K_2$ and $K_3$ using a single linear light-position sensor.

When the size of the light receiving surface 8 is limited and therefore the measurement range for measuring the eye refractive power is limited, it is desirable that the measurement range be variable. This may be achieved by making movable at least one of the light source 1 serving an index mark and the first lens 2 or at least one of the second lens 7 of the measuring optical system and the light-receiving surface 8.

In the above-shown embodiment, the semi-ring slot openings of the aperture stops 3 and 6 have been described to have the same outer diameter. This is because the light images of the aperture stops 3 and 6 are projected onto the eye to be examined E with the same projection magnification. However, as a modification, different projection magnifications may be used for different openings in such a manner that when the aperture stops 3 and 6 are projected on the eye E, the images of the openings formed there have the same outer diameter.

Obviously many other variations and modifications are possible in light of the above teachings.

I claim:

1. An eye refractometer comprising:
index mark forming means for providing a spot-like index mark;
a projection optical system for projecting the index mark onto a fundus of an eye to be examined through a first aperture stop disposed substantially optically conjugate with a pupil of the eye;
a measuring optical system for guiding a light beam of the index mark reflected by the eye fundus through a second aperture stop disposed substantially optically conjugate with the pupil of the eye, at least one of said first and second aperture stops having at least a semi-circular opening elongated in a circumferential direction around the center of the optical axis of said measuring optical system;

two-dimensional light detector means for receiving the light beam reflected by the eye fundus and for detecting the position of a continuously shaped image of the received light beam which is deformed from the shape of said elongated opening by the irregular distribution of the refractive power of the eye; and processing means for calculating the refractive power of the eye on the basis of the detection of the continuously shaped image of the light beam received by said two-dimensional light detector means.

2. An eye refractometer according to claim 1, wherein both of said first and second aperture stops each have a semi-circular ring type opening.

3. An eye refractometer according to claim 2, wherein said first and second aperture stops are symmetric about the optical axis.

4. An eye refractometer according to claim 2, wherein the images of the openings of said first and second aperture stops projected on the eye to be examined have the same outer diameter.

5. An eye refractometer according to claim 1, wherein the openings of said first and second aperture stops are so divided relative to the optical axis that the light can be guided to said measuring optical system through a mirror provided on one side of the divided openings.

6. An eye refractometer according to claim 1, wherein the index mark lies on the optical axis.

7. An eye refractometer comprising:
index mark forming means for providing a spot-like index mark;
a projection optical system for projecting the index mark onto a fundus of an eye to be examined through a first aperture stop disposed substantially optically conjugate with a pupil of the eye;
a measuring optical system for guiding a light beam of the index mark reflected by the eye fundus through a second aperture stop disposed substantially optically conjugate with the pupil of the eye, at least one of said first and second aperture stops having at least a semi-circular opening elongated in a circumferential direction around the center of the optical axis of said measuring optical system;
two-dimensional light detector means for receiving the light beam reflected by the eye fundus and for detecting the position of a continuously shaped image of the received light beam which is deformed from the shape of said elongated opening by the irregular distribution of the refractive power of the eye; and
monitor means for processing a signal generated by said two-dimensional light detector means and indicating the continuously shaped image of the received light beam.

8. An eye refractometer comprising:
index mark forming means for providing a spot-like index mark;
a projection optical system for projecting the index mark onto a fundus of an eye to be examined through a first aperture stop disposed substantially optically conjugate with a pupil of the eye;
a measuring optical system for guiding a light beam of the index mark reflected by the eye fundus through a second aperture stop disposed substantially optically conjugate with the pupil of the eye, at least one of said first and second aperture stops having at least a semi-circular opening elongated in a circumferential direction around the center of the optical axis of said measuring optical system;

two-dimensional light detector means for receiving the light beam reflected by the eye fundus and for detecting the position of a continuously shaped image of the received light beam which is deformed from the shape of said elongated opening by the irregular distribution of the refractive power of the eye;

processing means for calculating the refractive power of the eye on the basis of the detection of the continuously shaped image of the light beam received by said two-dimensional light detector means; and monitor means for indicating the continuously shaped image of the received light beam.

9. An eye refractometer comprising:
index mark forming means for providing a single index mark not extending in a fixed meridian direction;
a projection optical system for projecting the index mark onto a fundus of an eye to be examined through a first aperture stop disposed substantially optically conjugate with a pupil of the eye;
a measuring optical system for guiding a light beam of the index mark reflected by the eye fundus through a second aperture stop disposed substantially optically conjugate with the pupil of the eye, at least one of said first and second aperture stops having at least a semi-circular opening elongated in a circumferential direction around the center of the optical axis of said measuring optical system;

two-dimensional light detector means for receiving the light beam reflected by the eye fundus and for detecting the position of a continuously shaped image of the received light beam which is deformed from the shape of said elongated opening by the irregular distribution of the refractive power of the eye; and processing means for calculating the refractive power of the eye on the basis of the detection of the continuously shaped image of the light beam received by said two-dimensional light detector means.

10. An eye refractometer comprising:
index mark forming means for providing a single index mark not extending in a fixed meridian direction;
a projection optical system for projecting the index mark onto a fundus of an eye to be examined through a first aperture stop disposed substantially optically conjugate with a pupil of the eye;
a measuring optical system for guiding a light beam of the index mark reflected by the eye fundus through a second aperture stop disposed substantially optically conjugate with the pupil of the eye, at least one of said first and second aperture stops having at least a semi-circular opening elongated in a circumferential direction around the center of the optical axis of said measuring optical system;

two-dimensional light detector means for receiving the light beam reflected by the eye fundus and for detecting the position of a continuously shaped image of the received light beam which is deformed from the shape of said elongated opening by the irregular distribution of the refractive power of the eye; and monitor means for indicating the continuous shape of the received light beam.

11. An eye refractometer comprising:

index mark forming means for providing a single index mark not extending in a fixed meridian direction;

a projection optical system for projecting the index mark onto a fundus of an eye to be examined through a first aperture stop disposed substantially optically conjugate with a pupil of the eye;

a measuring optical system for guiding a light beam of the index mark reflected by the eye fundus through a second aperture stop disposed substantially optically conjugate with the pupil of the eye, at least one of said first and second aperture stops having at least a semi-circular opening elongated in a circumferential direction around the center of the optical axis of said measuring optical system;

two-dimensional light detector means for receiving the light beam reflected by the eye fundus and for detecting the position of a continuously shaped image of the received light beam which is deformed from the shape of said elongated opening by the irregular distribution of the refractive power of the eye;

processing means for calculating the refractive power of the eye on the basis of a signal generated by said two-dimensional light detector means representing the continuous shape of the light beam received by said two-dimensional light detector means; and monitor means for indicating the continuous shape of the received light beam.

* * * * *

UNITED STATES PATENT AND TRADEMARK OFFICE
CERTIFICATE OF CORRECTION

PATENT NO. : 4,952,049
DATED : August 28, 1990
INVENTOR(S) : Kazuhiro Matsumoto

It is certified that error appears in the above-identified patent and that said Letters Patent is hereby corrected as shown below:

On the title page, Item [54]

"EYE" should read --AN EYE--.

[56] References Cited:

"6018153 7/1983 Japan" should read --60-18153 7/1983 Japan--.

COLUMN 1:

Line 3, "EYE" should read --AN EYE--.

COLUMN 2:

Line 24, "EMBODIMENT" should read --EMBODIMENTS--.
Line 63, "objecive lens," should read --objective lens,--

COLUMN 3:

Line 6, "or" should read --of--.
Line 7, "semi ellipse" should read --semi-ellipse--.
Line 22, "processor 8," should read --processor 10,--.
Line 25, "semi-ring openings 3a, 6a" should read --semi-circular openings 3a, 6a--.
Line 61, "respect" should read --respect to--.

COLUMN 4:

Line 47, "D1." should read --D2.--.
Line 68, "direciton." should read --direction.--.

UNITED STATES PATENT AND TRADEMARK OFFICE
CERTIFICATE OF CORRECTION

PATENT NO. : 4,952,049  Page 2 of 2

DATED : August 28, 1990

INVENTOR(S) : Kazuhiro Matsumoto

It is certified that error appears in the above-identified patent and that said Letters Patent is hereby corrected as shown below:

COLUMN 5:

Line 40, "the F" should read --the ellipse F--.

COLUMN 6:

Line 41, "serving" should read --serving as--.
Line 53, "there" should read --thereon--.

Signed and Sealed this

Thirtieth Day of March, 1993

Attest:

STEPHEN G. KUNIN

Attesting Officer

Acting Commissioner of Patents and Trademarks